(12) United States Patent
Hwang et al.

(10) Patent No.: US 9,176,095 B2
(45) Date of Patent: *Nov. 3, 2015

(54) METHOD OF PROCESSING TARGET MATERIAL IN A SAMPLE

(71) Applicant: Samsung Electronics Co., Ltd., Suwon-si, Gyeonggi-do (KR)

(72) Inventors: Kyu-youn Hwang, Seoul (KR); Sung-hong Kwon, Yongin-si (KR); Joon-ho Kim, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 297 days.

This patent is subject to a terminal disclaimer.

(21) Appl. No.: 13/723,287

(22) Filed: Dec. 21, 2012

(65) Prior Publication Data
US 2013/0264205 A1     Oct. 10, 2013

(30) Foreign Application Priority Data
Apr. 6, 2012   (KR) ........................ 10-2012-0036243

(51) Int. Cl.
*G01N 1/34* (2006.01)
*G01N 27/447* (2006.01)
*G01N 1/28* (2006.01)
*C12N 1/06* (2006.01)
*B01L 3/00* (2006.01)

(52) U.S. Cl.
CPC ........ *G01N 27/44791* (2013.01); *B01L 3/5027* (2013.01); *C12N 1/066* (2013.01); *G01N 1/286* (2013.01); *B01L 2400/0481* (2013.01)

(58) Field of Classification Search
None
See application file for complete search history.

(56) References Cited

U.S. PATENT DOCUMENTS
6,406,605 B1   6/2002   Moles
7,312,611 B1   12/2007   Harrison et al.

FOREIGN PATENT DOCUMENTS
WO   WO 03/015923 A1   2/2003
WO   WO 2008/002462 A2   1/2008
WO   WO 2011/094577 A2   8/2011

OTHER PUBLICATIONS

Yu Chang Kim, J.H. Kang, S-J. Park, E-S. Yoon and J-K. Park, Microfluidic biomechanical device for compressive cell stimulation and lysis, 2007, Sensors and Actuators B, 128: 108-116.*
European Patent Office, Extended European Search Report in European Patent Application No. 13161604.7, Jul. 29, 2013, 4 pp.

* cited by examiner

*Primary Examiner* — Jill Warden
*Assistant Examiner* — Timothy G Kingan
(74) *Attorney, Agent, or Firm* — Leydig, Voit & Mayer, Ltd.

(57) ABSTRACT

An efficient method of processing a target material in a sample using a microfluidic device including an elastic membrane.

16 Claims, 8 Drawing Sheets

SEQUENCE LISTING

<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Synthetic (forward primer : MREJ type ii)

<400> SEQUENCE: 1
cgggttgtgt taattgaac                                              19

<210> SEQ ID NO 2
<211> LENGTH: 21
<212> TYPE: DNA
<213> ORGANISM: Artificial Sequence
<220> FEATURE:
<223> OTHER INFORMATION: Synthetic (reverse primer : MREJ type ii)

<400> SEQUENCE: 2
gaagcggctg aaaaaaccgc a                                           21

<210> SEQ ID NO 3
<211> LENGTH: 19
<212> TYPE: DNA
<213> ORGANISM: Artificial Sequence
<220> FEATURE:
<223> OTHER INFORMATION: Synthetic (forward primer : MREJ type v)

<400> SEQUENCE: 3
cgggttgtgt taattgaac                                              19

<210> SEQ ID NO 4
<211> LENGTH: 26
<212> TYPE: DNA
<213> ORGANISM: Artificial Sequence
<220> FEATURE:
<223> OTHER INFORMATION: Synthetic (reverse primer : MREJ type v)

<400> SEQUENCE: 4
taaaattacg gctgaaataa ccgcat                                      26

<210> SEQ ID NO 5
<211> LENGTH: 19
<212> TYPE: DNA
<213> ORGANISM: Artificial Sequence
<220> FEATURE:
<223> OTHER INFORMATION: Synthetic (forward primer : MREJ type xii)

<400> SEQUENCE: 5
cgggttgtgt taattgaac                                              19

<210> SEQ ID NO 6
<211> LENGTH: 32
<212> TYPE: DNA
<213> ORGANISM: Artificial Sequence
<220> FEATURE:
<223> OTHER INFORMATION: Synthetic (reverse primer : MREJ type xii)

<400> SEQUENCE: 6
acaatccgtt ttttagtttt atttatgata cg                               32

<210> SEQ ID NO 7
<211> LENGTH: 20
<212> TYPE: DNA
<213> ORGANISM: Artificial Sequence

```
<220> FEATURE:
<223> OTHER INFORMATION: Synthetic (TaqMan probe: 5' terminal is
      labelled with FAM and 3' terminal is labelled with BHQ1)

<400> SEQUENCE: 7
agagcattta agattatgcg                                                  20
```

METHOD OF PROCESSING TARGET MATERIAL IN A SAMPLE

CROSS-REFERENCE TO RELATED APPLICATIONS

This application claims the benefit of Korean Patent Application No. 10-2012-0036243, filed on Apr. 6, 2012, in the Korean Intellectual Property Office, the disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,803 Byte ASCII (Text) file named "711239_ST25.TXT," created on Dec. 20, 2012.

BACKGROUND

1. Field

The present disclosure relates to an efficient method of processing a target material in a sample.

2. Description of the Related Art

Since the concept of micro total analysis system (μTAS) was proposed by Andreas Manz, microfluidics-based biomolecule analysis has emerged as a promising approach to integrate complex analyte preparation and detection processes. μTAS can provide numerous advantages over conventional laboratory methods, such as ease-of-operation, increased detection sensitivity, low cost, and reduced time to result. μTAS utilizes the interaction between a liquid solution including target analyte and a solid surface because the analytical operations depend largely on the surface-based bioassays. Normally, these analysis devices perform the analytical processes to separate a target material to be assayed, such as a cell and/or a nucleic acid, from a patient's sample.

The most well-known method for carrying out such process is solid phase extraction (SPE), which involves capturing a target material to be analyzed, such as a cell and/or a nucleic acid on a solid, washing out the impurities, and eluting the target material. There have been various efforts to implement SPE on a micro device.

To capture a cell and/or a nucleic acid on a solid, a microstructure with a large surface area and a high surface-to-volume ratio (SVR) is employed to increase biomolecule capture efficiency and capacity.

The SPE microstructures with a large surface area and a high SVR are mostly in the form of micropillar or packed bead.

Micropillars may be implemented on a microchip with relatively high precision through conventional micro-electrical mechanical system (MEMS) technologies, deep dry etching technique, or the like. However, these processes are costly.

With regard to using beads, packing beads have been used in a capillary tube. However, it is difficult to check and verify close packing degree and to manufacture such a closely bead-packed capillary tube.

More advanced methods involve using a sol-gel material along with beads, or using an organic porous polymer structure along with beads.

These methods normally involve manufacturing a microchamber using glass, silicon, polymer, or the like, and packing the microchamber with beads. However, implementing close packing of the beads is difficult. Also, the use of the organic material makes the overall manufacturing process complicated and fails to ensure reproducibility.

SUMMARY

The disclosure provides a microfluidic device and an efficient method of processing a target material in a sample using the device.

According to an aspect of the present disclosure, the microfluidic device comprises a first chamber with at least one inlet and at least one outlet; a second chamber operatively connected with a pressure supply unit; and an elastic membrane disposed between the first chamber and the second chamber and forming a wall of at least part of the first and second chambers, wherein the first chamber comprises or contains a material that binds to a target material.

According to another aspect of the present disclosure, a method of processing a target material in a sample is provided, which includes introducing the sample into a first chamber of the microfluidic device, wherein at least one of the introducing of the sample and a subsequent operation is performed while the elastic membrane is extended toward the first chamber by applying a positive pressure to the second chamber, or while the elastic membrane is extended toward the second chamber by applying a negative pressure to the second chamber. In a related aspect, at least one of the introducing of the sample and a subsequent operation is performed while the elastic membrane is extended toward the first chamber by applying positive pressure to the second chamber, the sample material comprises a cell, the target material is a cell, nucleic acid, or a combination thereof, and the material binding to the target material is a material with a water contact angle of from about 70 degrees to about 95 degrees or a material having at least one amino group selected from among primary, secondary, tertiary, and quaternary amino groups. Also, the introducing of the sample is performed at a pH of from about 3.0 to about 6.0, and a salt concentration of from about 10 mM to about 500 mM, and the method further comprises introducing a cell lysis solution into the first chamber while the elastic membrane is extended toward the second chamber due to the application of negative pressure to the second chamber, thereby lysing the target material bound to the solid support. The method may further comprise introducing a washing solution into the first chamber after the lysis operation while the elastic membrane is extended toward the first chamber due to the application of positive pressure to the second chamber, thereby removing material that is not bound to the solid support; and introducing an eluent into the first chamber to release a nucleic acid from the first chamber including the solid support.

According to another aspect of the present disclosure, the target material is a nucleic acid, and the introducing of the sample is performed while the elastic membrane is extended toward the first chamber due to the applying of the positive pressure to the second chamber. Furthermore, the method comprises introducing a washing solution into the first chamber while the elastic membrane is extended toward the first chamber by applying a positive pressure to the second chamber, thereby removing a material that is not bound to the solid support; and introducing an eluent into the first chamber to release a nucleic acid from the solid support Additional aspects of the disclosed device and method will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
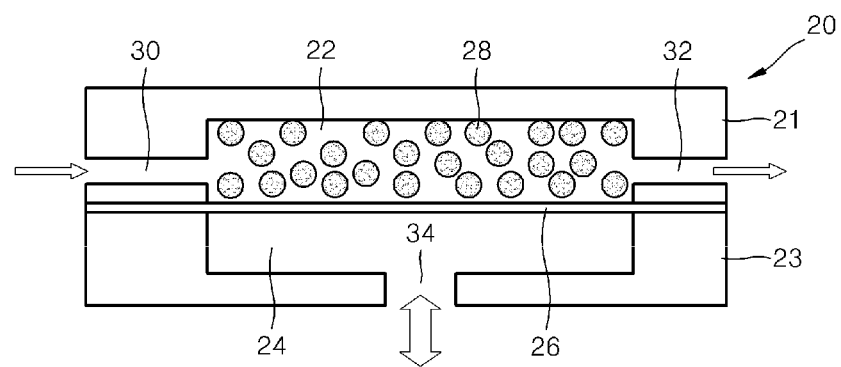
FIG. 1 is a cross-sectional views of a microfluidic device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. As used herein, the term "microfluidic device" may mean a device including at least one channel or chamber with a largest cross-sectional length in micrometers. For example, the microfluidic device may include at least one channel or chamber with a largest cross-sectional length of from about 1 μm to about 1000 μm.

According to an aspect of the present disclosure, a method of processing a target material in a sample includes introducing the sample into a first chamber of a microfluidic device, wherein the first chamber contains a solid support including a material that binds with the target material. The first chamber further includes an inlet and an outlet.

The microfluidic device also includes a second chamber operatively connected (e.g., fluidly connected) to a pressure supply unit, and an elastic membrane disposed between the first chamber and the second chamber, wherein the elastic membrane provides at least part of a wall of the first and second chambers. In other words, the elastic membrane separates at least a portion of the first chamber from at least a portion of the second chamber, such that applying positive pressure to the second chamber causes the elastic membrane to deflect and extend towards or into the first chamber, and applying negative pressure to the second chamber causes the elastic membrane to deflect and extend towards or into the second chamber.

At least one of the operation of introducing of the sample and a subsequent operation may be performed while the elastic membrane is extended toward the first chamber by applying a positive pressure to the second chamber, or while the elastic membrane is extended toward the second chamber by applying a negative pressure to the second chamber. The at least one operation may be performed in entire operation while the elastic membrane is extended toward the first chamber by applying a positive pressure to the second chamber, or while the elastic membrane is extended toward the second chamber by applying a negative pressure to the second chamber.

Furthermore, the inlet and outlet may be opened and closed, for instance, by providing valves or other closures at the inlet and/or outlet. In some embodiments, method includes introducing the sample into the first chamber via the inlet with the outlet either open or closed. The introduction of the sample via the inlet of the first chamber with the open outlet may be implemented, for example, by continuously flowing the sample from the inlet through the outlet, and passing through the first chamber. Therefore, at least one of the introducing of the sample and a subsequent operation may be implemented by flowing the sample from the inlet of the chamber through the outlet in a continuous or periodic manner.

A sample can be passed through the first chamber from the inlet to the outlet at any suitable flow rate. For example, a flow rate of the sample may be from about 10 microliters per minute (μl/min) to about 500 μl/min, and in some embodiments, may be from about 20 μl/min to about 500 μl/min, from about 50 μl/min to about 500 μl/min, from about 75 μl/min to about 500 μl/min, from about 100 μl/min to about 500 μl/min, from about 200 μl/min to about 500 μl/min, from about 300 μl/min to about 500 μl/min, or from about 400 μl/min to about 500 μl/min. The introduction of the sample into the first chamber may be performed under conditions that are appropriate for the target material to bind to the material in the solid support.

The introducing of the sample into the first chamber may be performed by any suitable technique, for example, by applying a positive pressure to the inlet and/or applying a negative pressure to the outlet. The subsequent process following the introducing of the sample may be at least one of washing, drying, and elution. The washing may include contacting the solid support of the first chamber with a washing solution to remove unbound material including material only weakly bound to the solid support so as to be removed by the washing solution (e.g., impurities). The washing may be performed under conditions whereby the target material bound to the solid support is not substantially removed. The drying may be performed to dry the solid support by flowing gas, for example, air, from the inlet of the first chamber to the outlet. The elution may involve contacting the solid support with an eluent to separate the target material from the solid support. For example, the elution may include contacting the solid support with a cell eluent in a condition that is appropriate to separate cells from the solid support. A different eluent may be used when the target is a different type of biomaterial (e.g., a nucleic acid eluent for nucleic acid targets, a protein eluent for protein targets, etc.).

The sample may be any of a variety of materials including a target material. The target material may be a biological or non-biological material. The biological material may be, for example, a material derived from a virus or a living organism. The biological material may be, for example, a cell or a cell component. The cell may be a eukaryote or a prokaryote, for example, a gram-positive or gram-negative bacteria cell. The biological cell component may be, for example, protein, sugar, lipid, nucleic acid, or a combination thereof. The sample comprising the target material may include, for example, blood, urine, a mucosa swab (for example, a nasal swab), body fluid, tissue, a biological sample, or a combination thereof.

The material that binds to the target material may specifically or non-specifically bind to the target material. Specific binding of the target material is associated in a broad sense with the relationship between a ligand and a receptor, an antigen and an antibody, an enzyme and a substrate or inhibitor, and the like. Thus, the material that specifically binds to the target material may selectively bind to the target material to the substantial exclusion of other materials in a sample. Examples of materials that specifically bind a target include, for instance, an antibody, an antigen, a substrate, an inhibitor, a receptor, a ligand, or a combination thereof.

Non-specifically binding materials may be used to capture or separate target materials on the basis of chemical or physical properties. For example, a material having a certain hydrophobicity may be used. Such an embodiment may be useful, for instance, when the target material is a cell or a nucleic acid, particularly a bacterial cell. For instance, the non-specifically binding material may be a material with a water contact angle of from about 70 degrees to about 95 degrees, or a material or compound having at least one surface amino group (e.g., a plurality of surface amino groups) selected from among primary, secondary, tertiary, and quaternary amino groups. The tertiary amino group may be any of a variety of tertiary amino groups excluding an amide group and a nitrile group. Amino groups can be introduced on a surface by immobilizing an aminosilane moiety. The aminosilane moiety may be provided by deposition of aminosilane molecules on a surface of the solid support. The aminosilane molecules may be an organic aminosilane molecule represented by the formula of $(X_1)(X_2)(X_3)Si(Y)$, wherein $X_1$, $X_2$, and $X_3$ may each be independently selected from the group consisting of a hydrogen atom, an alkoxy group (—OR), and a halogen atom. Further, at least one of $X_1$, $X_2$, and $X_3$ may be an alkoxy group. In the alkoxy group (—OR), R may be a C1-020 hydrocarbonyl group (e.g., branched or straight chain C1, C2, C3, C4, C5, C6, C7, C8, C9, C10, C11, C12, C13, C14, C15, C16, C17, C18, C19, or C20 hydrocarbonyl group), for example, methyl, ethyl, propyl, isopropyl, butyl, pentyl, or the like. The halogen atom may be, for instance, fluorine (F), chlorine (Cl), bromine (Br), iodine (I), or astatine (At). Y may be an organic moiety with at least one amino group, for example, amino alkyl or polyethyleneimine. The aminoalkyl may include a C1-020 alkyl group (e.g., branched or straight chain C1, C2, C3, C4, C5, C6, C7, C8, C9, C10, C11, C12, C13, C14, C15, C16, C17, C18, C19, or C20 alkyl group). The polyethyleneimine may be represented by the formula of —[$CH_2CH_2NH$]n-, where n is from 2 to 100. The alkoxy group (—OR) may be hydrolyzed in an aqueous condition, producing hydroxyl groups of which at least one may take part in condensation and elimination reactions with —OH group found on the surface of the solid support and the surface of adjacent silane molecule. The aminosilane molecule may be, for example, 3-aminopropyltriethoxysilane (GAPS), or polyethyleneiminetriethoxysilane such as N-(2-aminoethyl)-3-aminopropyltriethoxysilane (EDA) and (3-trimethoxysilyl-propyl) diethylenetriamine (DETA). Alternatively, the hydrophobic material may include polyethyleneimine (PEIM), octadecyldimethyl (3-trimethoxysilyl propyl) ammonium chloride (OTC) or tridecafluorotetrahydrooctyl trimethoxysilane (DFS). The aminosilane or other hydrophobic molecules or materials may be coated on the solid support using a known method, for example, using dip coating, spin coating, or chemical vapor deposition (CVD). The solid support may be inside the first chamber, not bound to the wall of the first chamber.

As used herein, the water contact angle may be measured, for example, on a Krüss drop-shape analysis system (Type DSA 10 Mk2, Kruss, Germany). A droplet of 1.5 uL deionized water was placed on the sample. The droplet was monitored every 0.2 seconds for a period of 10 seconds by a charge-coupled device (CCD) camera and analyzed by Drop-Shape Analysis (DSA) software (DSA version 1.7, Kruss). The complete profile of the droplet was fitted by the tangent method to a general conic section equation. The angles were determined at both the right and left sides. An average value was calculated for each drop and a total of five drops per sample were measured. The average of the angles of the five drops was taken as the contact angle.

The first chamber and/or second chamber may have any suitable volume. Since the elastic membrane separates the first and second chamber, and forms at least part of the wall of the first and second chamber, the volume of the first and second chamber may change as positive or negative pressure is applied to the second chamber, causing the elastic membrane to deflect towards (into) or away from the first chamber. When no positive pressure or negative pressure is applied to the second chamber, leaving the elastic membrane in a neutral position, the volume of the first and/or second chamber may be, for example, from about 1 ul to about 500 ul, and in some embodiments, may have a volume of from about 1 ul to about 500 ul, from 10 ul to about 500 ul, from about 20 ul to about 500 ul, from about 50 ul to about 500 ul, from about 75 ul to about 500 ul, from about 100 ul to about 500 ul, from about 200 ul to about 500 ul, from about 300 ul to about 500 ul, from about 400 ul to about 500 ul, from about 1 ul to about 400 ul, from about 1 ul to about 300 ul, from about 1 ul to about 200 ul, from about 1 ul to about 100 ul, from about 10 ul to about 100 ul, from about 20 ul to about 100 ul, from about 50 ul to about 100 ul, or from about 75 ul to about 100 ul.

The elastic membrane may be moveable toward the first chamber and/or the second chamber; and sustained in position for a period of time, for example, for an entire operation or entire operations, or may vibrate as a positive pressure or a negative pressure is applied to the second chamber (e.g., as positive pressure or negative pressure is repeatedly applied or sequentially applied, or as a positive or negative pressure is varied so as to cause the membrane to vibrate), for example, while the equilibrium point for an oscillation is located in a position in the first chamber or the second chamber. That is, the elastic membrane at a resting position may be extended toward the first chamber or the second chamber. The elastic membrane may comprise any suitable material, for example, polydimethylsiloxane (PDMS), polypropylene, polycarbonate, polymethylmethacrylate (PMMA), Teflon, silicones, polyurethane, polyethylene, polystyrene, or a combination thereof. The elastic membrane may have any suitable thickness that allows the membrane to be moveable toward the first chamber and/or the second chamber or to vibrate as a positive pressure or a negative pressure is applied to the second chamber. The thickness of the elastic membrane may be appropriately selected according to an elastic material used. The elastic membrane may have 10 GPa or less Young's modulus. The elastic membrane may have a thickness of, for example, from about 10 μm to about 5000 μm, and in some embodiments, may have a thickness of from about 10 μm to about 1000 μm, from about 50 μm to about 1000 μm, from about 100 μm to about 1000 μm, from about 200 μm to about 1000 μm, from about 300 μm to about 1000 μm, from about 400 μm to about 1000 μm, from about 500 μm to about 1000 μm, from about 700 μm to about 1000 μm, from about 10 μm to about 900 μm, from about 50 μm to about 800 μm, from about 100 μm to about 700 μm, from about 200 μm to about 600 μm, or from about 200 μm to about 500 μm.

The pressure supply unit may be any unit that can provide positive or negative pressure to the second chamber, such as a pneumatic pump. The pressure supply unit may be operatively connected to a pressure controller for periodically or non-periodically and continuously or discontinuously supplying a positive pressure, a negative pressure, or a combination thereof to the second chamber. The pressure supply unit may supply a controlled pressure to the second chamber so that the elastic membrane may be extended, for example for the entire period of an operation, according to the controlled pressure. For example, the elastic membrane may be extended toward the second chamber if a positive pressure is applied, or may be extended toward the second chamber if a negative pressure is applied. If a combination of the positive and negative pressures is applied in sequence (or if positive or negative pressure is repeated applied (e.g., pulsed) or if the magnitude of the pressure applied is rapidly varied), the elastic membrane may vibrate as compared to a resting position in which no pressure is applied to the second chamber or an extended position achieved by a static application of positive or negative pressure. The vibration may induce a solid support collision in the first chamber. This collision may induce the sample or target material bound to the solid support to be processed, for example, to be lyzed if the sample or target material is a cell. The collision may also facilitate interaction between a solution and the solid support. The elastic membrane may vibrate while being extended toward the first chamber or the second chamber in relation to the resting position, thereby in a reduced or increased surface-to-volume ratio (SVR), the SVR indicating a ratio of the surface area of the solid support to the volume of the first chamber.

In the above-described method of processing a target material in a sample, the pressure controller may include a storage medium storing a signal or program for controlling application of a positive pressure to the second chamber to extend the elastic chamber toward the first chamber, or application of a negative pressure to the second chamber to extend the elastic membrane toward the second chamber at any give step in the method, for instance, during or immediately after introducing a sample into the first chamber or during a subsequent operation. For example, when the sample includes a cell, the storage medium may store a signal or program for applying a positive pressure to the second chamber to extend the elastic membrane toward the first chamber in a sample introduction operation and a washing operation, and a signal for enabling application of a negative pressure to the second chamber to extend the elastic membrane toward the second chamber in a cell lysis operation.

In some embodiments, when the sample includes a nucleic acid, protein, or sugar as the target material, the storage medium may store a signal or program for applying a positive pressure to the second chamber to extend the elastic membrane toward the first chamber in a sample introduction operation, a washing operation, and a target material elution operation.

The storage medium may further store a signal or program for enabling application of a positive pressure to the second chamber to extend the elastic membrane toward the first chamber, or application of a negative pressure to the second chamber to extend the elastic membrane toward the second chamber, and a signal for inducing a variation in pressure so that the elastic membrane vibrates while being extended toward the first or second chamber.

Thus, the method may further include controlling a pressure of the second chamber according to a pressure control signal stored in the storage medium. The controlling of the pressure of the second chamber may be performed by a microprocessor, which may be operatively connected to the storage medium. The storage medium may be readable by the microprocessor.

The solid support may be hard enough to use as a cell lysis means. The hard solid support may be formed of a solid material or may be coated with a solid material. The phrase "hard enough" refers to a hardness sufficient to destroy a cell membrane, cell wall, an envelope of a virus, or a combination thereof to release contents thereof. The support may be a magnetic or non-magnetic solid support. The solid support may be implemented as any form of solid support, such as spheres, or non-spheres including plates, or beads formed of at least one of glass, metal, and metal oxide. The metal oxide may be, for example, $ZrO_2$, $SiO_2$, $Al_2O_3$, $Fe_2O_3$, $TiO_2$, or a mixture thereof, such as a mixture of $ZrO_2$ and $SiO_2$. The metal solid supports may include, for example, steel beads or stainless steel beads.

The solid support is not limited to microscale dimensions, and may have any dimensions by which the sample can be processed, for instance, cell lysis performed, by operation of the above-described device. For example, the largest cross-sectional width of the solid support may be from about 10 nanometers (nm) to about 1000 micrometers (μm), and in some embodiments, may be from about 10 nm to about 500 μm, and in some other embodiments, may be from about 100 nm to about 100 μm, and in still other embodiments, may be from about 1 μm to about 500 μm. The solid support may be, for example, spherical, planar, or multi-planar. In some embodiments, a plurality of solid supports may be disposed in the first chamber. The number of the solid supports in the first chamber may be, for example, two or greater, 10 or greater, 100 or greater, 1,000 or greater, 10,000 or greater, 100,000 or greater, or $10^8$ or greater. According to various examples, the number of the solid supports in the first chamber may be about 1 to $10^8$, about 10 to $10^8$, about 100 to $10^8$, about 1,000 to $10^8$, about $10^4$-$10^8$, about $10^5$ to $10^8$, about $10^6$ to $10^8$, about $10^7$ to $10^8$, about 10 to $10^7$, about 100 to $10^7$, about 1,000 to $10^7$, about $10^4$ to $10^7$, about $10^5$ to $10^7$, or about $10^6$ to $10^7$. The solid support may be previously introduced into the first chamber during manufacture of the first chamber so as not to pass out through the inlet or outlet of the first chamber. The solid support may have a density (D) of greater than 1 grams per centimeter-cubed ($g/cm^3$), and in some embodiments, may be about 1 $g/cm^3$ to about 20 $g/cm^3$.

In addition to the solid support, at least one of a wall of the first chamber may be formed of a binding material able to bind to a target material. The wall of the first chamber may comprise a target-binding material that is the same or different from that of the solid support, and which may bind (specifically or non-specifically) a target material that is different from or the same as the target material to which the solid support binds. Suitable target materials include any of those materials previously described, for example, cells or viruses, or other biomaterials or biomolecules. The binding material may include a material that specifically binds to a target or a material that non-specifically binds a target. The materials that specifically and non-specifically bind a target material may include any of those materials previously described herein with respect to the target-binding material of the solid support.

In some embodiments, in the microfluidic device, the second chamber may include a plurality of sub-chambers operatively connected to the pressure supply unit, where the elastic membrane may be disposed between the first chamber and the sub-chambers of the second chamber, and may form a wall of at least part of the first chamber and each sub-chamber of the second chamber.

A positive pressure applied to the second chamber may move the elastic membrane toward the first chamber so that the solid support in the first chamber may remain having a constant surface area with a reduced volume. That is, the solid support may have an increased ratio of the surface area of the solid support to the volume of the first chamber (hereinafter, "surface-to-volume ratio (SVR)"). The above-described method may include applying a positive pressure to the second chamber while at least one of the inlet and outlet is open, to increase the SVR. According to various examples, the positive pressure that is applied to the second chamber may be determined to lead to an SVR of 0.05 $\mu m^{-1}$ or greater, to an SVR of 0.11 $\mu m^{-1}$ or greater, 0.12 $\mu m^{-1}$ or greater, 0.13 $\mu m^{-1}$ or greater, 0.14 $\mu m^{-1}$ or greater, or 0.15 $\mu m^{-1}$ or greater. In some other embodiments, the positive pressure that is applied to the second chamber may be determined to lead to an SVR of from about 0.05 $\mu m^{-1}$ to about 0.15 $\mu m^{-1}$, from about 0.11 $\mu m^{-1}$ to about 0.15 $\mu m^{-1}$, from about 0.12 $\mu m^{-1}$ to about 0.15 $\mu m^{-1}$, from about 0.13 $\mu m^{-1}$ to about 0.15 $\mu m^{-1}$, from about 0.14 $\mu m^{-1}$ to about 0.15 $\mu m^{-1}$, from about 0.10 $\mu m^{-1}$ to about 0.14 $\mu m^{-1}$, from about 0.11 $\mu m^{-1}$ to about 0.14 $\mu m^{-1}$, from about 0.12 $\mu m^{-1}$ to about 0.14 $\mu m^{-1}$, or from about 0.13 $\mu m^{-1}$ to about 0.14 $\mu m^{-1}$. A negative pressure applied to the second chamber may move the elastic membrane toward the second chamber so that the solid support in the first chamber may remain having a constant surface area with an increased volume. That is, the solid support may have a reduced ratio of the surface area of the solid support to the volume of the first chamber (SVR). The above-described method may include applying a negative pressure to the second chamber while at least one of the inlet and outlet is open, to reduce the SVR. A positive pressure, a negative pressure or a combination thereof applied to the second chamber may vibrate the elastic membrane. A level of the positive pressure or negative pressure may be appropriately selected depending on the type and thickness of the elastic membrane. In some embodiments, if the elastic membrane is a PDMS membrane having a thickness of from about 200 μm to about 300 μm, the positive pressure may be from about 10 pascal (Pa) to about 300 kPa, for example, from about 30 Pa-300 kPa, from about 50 Pa-300 kPa, from about 70 Pa-300 kPa, from about 80 Pa-300 kPa, from about 200 Pa-300 kPa, from about 10 Pa-200 kPa, from about 30 Pa-150 kPa, or from about 50 Pa-100 kPa.

In the above-described method, at least one of the introduction of the sample and a subsequent operation may be performed while only a positive pressure is applied to the second chamber. That is, each operation may be performed after stopping applying of a positive pressure or without application of a negative pressure.

In some embodiments, the target material or sample may comprise a cell, wherein the above-described method may further include vibrating the elastic membrane to lyse the cell. The cell may be a bacterial cell, which may be, for example, a gram-positive or gram-negative cell. The vibrating may be implemented by applying a positive pressure, a negative pressure, or a combination thereof to the second chamber.

In some embodiments, the elastic membrane may be vibrated at a frequency of about 0.001 hertz (Hz) to about 100 kilohertz (kHz). In some other embodiments, the elastic membrane may be vibrated to a frequency of about 0.01 Hz to about 100 kHz, a frequency of about 0.1 Hz to about 100 kHz, a frequency of about 1 Hz to about 100 kHz, a frequency of about 5 Hz to about 100 kHz, or a frequency of about 10 Hz to about 100 kHz. The pressurizing may be performed using means for providing a driving force operatively connected to at least one of the inlet and the outlet to provide a driving force for inflowing and discharging fluid. The driving force providing means may be any device able to induce motion of fluid, and in some embodiments, may be a device able to apply a positive pressure or a negative pressure to the second chamber, such as a pump. The pump may be a micropump implementable in a microfluidic device. The micropump may be a mechanical or non-mechanical device. A mechanical microfluidic pump may in general include an actuator and a moving part, which may be a membrane or a flap. Driving power of the mechanical microfluidic pump may be generated, for example, using piezoelectric, electrostatic, thermo-pneumatic, pneumatic, or magnetic effects. A non-mechanical pump may function by, for example, generation of electro-hydrodynamic, electro-osmotic, or ultrasonic flow.

In some embodiments, the target material or sample may comprise a cell, where the method may further include introducing a cell lysis solution into the first chamber while the elastic membrane is extended toward the second chamber, for example, with an SVR of about 0.05 $\mu m^{-1}$ or less, by applying a negative pressure to the second chamber after the introducing of the sample, thereby lysing the target material bound to the solid support. The cell may be a bacterial cell, which may be, for example, a gram-positive or gram-negative cell. The introducing of the cell lysis solution may be performed while the outlet of the first chamber is closed. In this regard, the method may further include closing the inlet after the introduction of the sample. However, since there is a space for blocking discharge of the cell lysis solution through the open outlet while the elastic membrane is extended toward the second chamber, it may be possible to introduce the cell lysis solution with the outlet not closed. Therefore, according to an embodiment of the present disclosure, the method may include introducing a cell lysis solution while the outlet of the first chamber is not closed. The cell lysis solution may include any cell lytic material. For example, the cell lysis solution may include a specific cell lytic material including an enzyme such as lysozyme, or a non-specific cell lytic material such as a surfactant. Non-limiting examples of the non-specific cell lytic material are a NaOH solution, a KOH solution, or a combination thereof. The introducing of the cell lytic solution may be performed with the elastic membrane extended toward the second chamber, i.e., while the first chamber has a lower SVR than in relation to a resting position, to lower fluidic resistance caused from the solid support and facilitate control of a small amount of solution.

In this regard, the method may further include vibrating the elastic membrane after the introducing of the cell lysis solution, to facilitate cell lysis. The vibration may be induced by applying a positive pressure, a negative pressure, or a combination thereof. The vibration may induce solid support collision in the solid support in the first chamber. The collision may facilitate processing of the target material bound to the solid support, for example, cell lysis, if the target material is a cell.

In some embodiments, the elastic membrane may be vibrated at a frequency of about 0.001 Hz to about 100 kHz. In some other embodiments, the elastic membrane may be vibrated at a frequency of about 0.01 Hz to about 100 kHz, a frequency of about 0.1 Hz to about 100 kHz, a frequency of about 1 Hz to about 100 kHz, a frequency of about 5 Hz to about 100 kHz, or a frequency of about 10 Hz to about 100 kHz. The pressurizing may be performed using a driving force providing means operatively connected to at least one of the inlet and the outlet to provide a driving force for inflowing to and/or discharging fluid from the second chamber. The driving force providing means may be any device able to induce motion of fluid, and in some embodiments, may be a device able to apply a positive pressure or a negative pressure to the second chamber, such as a pump. The pump may be, for example, a micropump implementable in a microfluidic device. As used herein, the terms "microfluidic device" and "micropump" may mean a device including at least one channel or chamber with a largest cross-sectional length in micrometers. For example, the microfluidic device may include at least one channel or chamber with a largest cross-sectional length of from about 1 μm to about 1000 μm. The micropump may be a mechanical or non-mechanical device. A mechanical microfluidic pump may in general include an actuator and a moving part, which may be a membrane or a flap. Driving power of the mechanical microfluidic pump may be generated using piezoelectric, electrostatic, thermopneumatic, pneumatic, or magnetic effects. A non-mechanical pump may function by, for example, generation of electro-hydrodynamic, electro-osmotic, or ultrasonic flow.

In some embodiments, the method may further include, before the lysis operation, applying a positive pressure to the second chamber to introduce a washing solution into the first chamber with the elastic membrane extended toward the first chamber, thereby removing a material remaining unbound to the solid support or a weakly bound material (impurities). The elastic membrane may be vibrated while being extended toward the first chamber. For example, during the washing operation, a variation in pressure of the second chamber may be induced while a positive pressure is applied to the second chamber with the elastic membrane extended toward the first chamber, thereby vibrating the elastic membrane to increase washing efficiency. Furthermore, a vibration frequency may be adjusted to control the amount and/or type of a material removed by the washing. That is, washing stringency may be adjusted.

In some embodiments, the method may further include, after the washing operation, flowing a gas from the inlet of the first chamber through to the outlet while the elastic membrane is extended toward the first chamber by applying a positive pressure to the second chamber, thereby drying the solid support. The gas may be air or nitrogen.

In some embodiments, the material binding to the target material may be a material with a water contact angle of from about 70 degrees to about 95 degrees or a material having at least one amino group selected from among primary, secondary, tertiary, and quaternary amino groups. The material may bind to bacterial cells, viruses, biomolecules, or a combination thereof. The biomolecules may be, for example, a protein, a nucleic acid, a sugar, or a combination thereof. The lysis operation may be performed in a NaOH solution. Introduction of the NaOH solution may lyze the cell and release a nucleic acid from the cell. Afterward, the NaOH solution may be recovered to obtain a solution including the isolated nucleic acid.

In some embodiments, the method may further include introducing an eluent into the first chamber while the elastic membrane is extended toward the first chamber by applying a positive pressure to the second chamber, thereby releasing a nucleic acid from the first chamber including the solid support or from the solid support. The releasing of the nucleic acid may be performed under conditions in which the nucleic acid can be separated from the solid support. Such conditions may be easily selected by one of ordinary skill in the art. Non-limiting examples of the eluent are a biochemical buffer such as phosphate buffered saline, water, saline, a Tris buffer, a NaOH solution, and a KOH solution.

According to another aspect of the present disclosure, a method of processing a target material in a sample includes introducing the sample into a first chamber of a microfluidic device, where the first chamber includes a solid support including a material bindable with the target material, to bind the target material to the solid support. The microfluidic device includes the first chamber with an inlet and an outlet, a second chamber operatively connected with a pressure supply unit, and an elastic membrane disposed between the first chamber and the second chamber and forming a wall of at least part of the first and second chambers. In some embodiments, at least one of the operation of introducing of the sample and a subsequent operation is performed while the elastic membrane is extended toward the first chamber by applying a positive pressure to the second chamber, the target material is a cell, and the material binding to the target material is a material with a water contact angle of from about 70 degrees to about 95 degrees or a material having at least one amino group selected from among primary, secondary, tertiary, and quaternary amino groups, and the introduction of the sample is performed at a pH of from about 3.0 to about 6.0, and a salt concentration of from about 10 millimole (mM) to about 500 mM, for example, about 10 mM to about 400 mM, about 10 mM to about 300 mM, about 10 mM to about 200 mM, about 10 mM to about 150 mM, about 10 mM to about 100 mM, about 10 mM to about 50 mM, about 30 mM to about 500 mM, about 30 mM to about 400 mM, about 30 mM to about 300 mM, about 30 mM to about 200 mM, about 30 mM to about 150 mM, about 30 mM to about 100 mM, about 30 mM to about 50 mM; introducing a washing solution into the first chamber while the elastic membrane is extended toward the first chamber by applying a positive pressure to the second chamber, thereby removing a material remaining unbound to the solid support or a weakly bound material. The method further includes introducing a cell lysis solution into the first chamber while the elastic membrane is extended toward the second chamber by applying a negative pressure to the second chamber, thereby lysing the target material bound to the solid support; and introducing an eluent into the first chamber to release a nucleic acid from the first chamber including the solid support or the solid support. The introducing an eluent may be performed while the elastic membrane is extended toward the first chamber by applying a positive pressure to the second chamber.

In some embodiments, a method of processing a target material in a sample, includes introducing the sample into a first chamber of a microfluidic device, where the first chamber includes a solid support including a material bindable with the target material, to bind the target material to the solid support. The microfluidic device includes the first chamber with an inlet and an outlet, a second chamber operatively connected with a pressure supply unit, and an elastic membrane disposed between the first chamber and the second chamber and forming a wall of at least part of the first and second chambers, where the target material is a nucleic acid, and the introducing of the sample is performed while the elastic membrane is extended toward the first chamber due to the applying of the positive pressure to the second chamber. The method further includes introducing a washing solution into the first chamber while the elastic membrane is extended toward the first chamber by applying a positive pressure to the second chamber, thereby removing a material remaining unbound to the solid support or a weakly bound material; and introducing an eluent into the first chamber to release a nucleic acid from the solid support. The introducing an eluent may be performed while the elastic membrane is extended toward the first chamber due to the applying of the positive pressure to the second chamber.

In above embodiment, the material binding to the target material may be any known material capable of binding to a nucleic acid, which may specifically or non-specifically bind to the nucleic acid. Non-limiting examples of the material capable of binding to a nucleic acid are metal oxide, a material with an electrically positive functional group, a material with an electrically negative functional group, or a material with both electrically positive and negative functional groups. The metal oxide may include, for example, one of $ZrO_2$, $SiO_2$, $Al_2O_3$, $Fe_2O_3$, $TiO_2$, or a mixture thereof. The electrically positive functional group may be a primary, secondary, tertiary or quaternary amino group. The electrically negative functional group may be, for example, a carboxyl group. The material capable of binding to a nucleic acid may bind with, for example, a nucleic acid, in a chaotropic salt solution, kosmotropic salt solution, or a buffer, for example, a biochemical buffer, including a material capable of facilitating binding with a nucleic acid, such as polyethylene glycol, thereby optimizing the binding reaction. The sample may include, for example, a cell lysate or a lyzed virus product.

In some embodiments, the washing solution may selectively remove a material remaining unbound to the solid support or a weakly bound material (for example, impurities), and not substantially remove a nucleic acid bound to the solid support. The washing solution and a washing condition may include, for example, water, a saline, or a buffer such as a PBS or Tris buffer In some embodiments, the eluent may be any known solution capable of releasing a nucleic acid bound to the solid support, for example, water, or a buffer such as a PBS or Tris buffer. The eluent and an elution condition may be appropriately selected by one of ordinary skill in the art. The elution of the nucleic acid may be adjusted according to the purpose thereof, through optimization of the eluent's conditions, such as salt concentration, pH and the like of the used eluent. In the present embodiment the same elements as those described in the previous embodiments are not described to avoid redundancy.

FIG. 1 is a sectional view of a microfluidic device 20, according to an embodiment of the present disclosure that may be compatible with the above-described method of processing a target material in a sample. Referring to FIG. 1, the microfluidic device 20 includes an upper plate 21, a lower plate 23, and a membrane 26. The membrane 26 is disposed between the upper plate 21 and the lower plate 23. A spatial region of the upper plate 21 forms a first chamber 22, and a spatial region of the lower plate 23 forms a second chamber 24. The first and second chambers 22 and 24 are separated by the membrane 26 disposed therebetween. In other words, the first chamber 22 is a space delimited by the upper plate 21 and the membrane 26, and the second chamber 24 is a space delimited by the lower plate 23 and the membrane 26.

The membrane 26 may be flexible or elastic. The membrane 26 may be a polymer membrane such as, for example, a polydimethylsiloxane (PDMS) membrane. The membrane 26 may have a thickness of, for example, from about 1 μm to about 5 mm. The first chamber 22 may include one or more solid supports. The embodiment of FIG. 1 illustrates a plurality of microparticles 28 used as the solid support. Since the first chamber 22 is delimited by the membrane 26, the microparticles 28 in the first chamber 22 may contact the membrane 26. The microparticles 28 may have a diameter of, for example, from about 1 μm to about 1,000 μm. A density (D) of the microparticles 28 in the first chamber 22 may be greater than 1 $g/cm^3$, and in some embodiments, may be from about 1 $g/cm^3$ to about 20 $g/cm^3$. More than one microparticle may be included per 1 μL of a liquid medium, and in some embodiments, there may be about 10, 100, 1000, 10000, or $10^9$ or greater microparticles per 1 μL of the liquid medium. The microparticles 28 in the first chamber may be about 1 to about $10^8$ in number per 1 μL of the liquid medium, and in some other embodiments, may be from about 100 to about $10^6$ in number per 1 μL of the liquid medium. The microparticles 28 may include glass beads. The microparticles 28 may be, for example, metal oxide beads or metallic beads. The metal oxide may include, for example, one of $ZrO_2$, $SiO_2$, $Al_2O_3$, $Fe_2O_3$, $TiO_2$, and a mixture thereof. The mixture may be, for example, a mixture of $ZrO_2$ and $SiO_2$. The metallic beads may include, for example, steel beads or stainless steel beads. If the microparticles 28 have a composition of glass or metal oxide, a surface modification for cell or nucleic acid capture may be facilitated.

The microfluidic device 20 includes an inlet 30 and an outlet 32. The inlet 30 and the outlet 32 may have a diameter smaller than that of the solid support (e.g. microparticles 28). A solution including cells to be disrupted or nucleic acid to be purified is introduced into the first chamber 22 through the inlet 30. The resulting product of disruption of cell membranes and/or walls, including a nucleic acid, and the like, or purified nucleic acid is released through the outlet 32. The inlet 30 penetrates one wall of the upper plate 21 and is connected to one side of the first chamber 22. The outlet 32 penetrates another wall of the upper plate 21 and is connected to the other side of the first chamber 22.

The second chamber 24 may be a pneumatic chamber including a space into which a fluid, such as for example air, pressing periodically or non-periodically on the membrane 26 is introduced. High-pressurized fluid is introduced into the second chamber 24, pressing the membrane 26. When pressed, the membrane 26 may protrude toward the first chamber 22, reducing the specific volume of the first chamber 22. On the other hand, when a negative pressure is provided, the membrane 26 may protrude toward the second chamber 24. The second chamber 24 may have a port 34 as an inflow and outflow passage for fluid pressurizing or depressurizing the interior of the second chamber 24. As the fluid is periodically or non-periodically introduced into or released from the second chamber 24 through the port 34, the membrane 26 may be periodically or non-periodically vibrated. The vibration of the membrane 26 may eventually periodically or non-periodically pressurize the microparticles 28 in the first chamber 22 by direct contact with the microparticles 28 or via the solution in the first chamber 22. As a result, the microparticles 28 are induced to move, colliding against each other or against an inner wall of the first chamber 22 during the motion. Due to the motion of the microparticles 28, the cells introduced into the interior of the first chamber 22 are disrupted by being sheared or grinded. In addition, the interaction of target material such as, for example, cells or biomolecules with surrounding liquid solution is increased. The pressurizing or depressurizing of the interior of the second chamber 24 by the supply or release of the fluid into or out of the second chamber 24 may be arbitrarily controlled to lead to a vibration frequency of the membrane 26 ranging from about 0.001 Hz to about 100 kHz.

Figure 2:
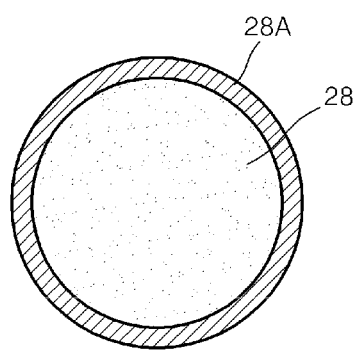
FIG. 2 is a sectional view of a bead with a cell- or nucleic acid-capturing organic or inorganic layer on its surface.

As illustrated in FIG. 2, the microparticles 28 may have a material 28A capable of specifically or non-specifically binding to a target material on surfaces thereof, for example, a material capable of capturing cells. For example, to selectively capture a specific cell, an antibody, an aptamer, or the like may be coated on the surfaces of the microparticles 28. A non-specific cell may be captured by the action of a hydrophobic or electrostatic force. In some embodiments, the material 28A capable of binding to the target material may be a material with a water contact angle of from about 70 degrees to about 95 degrees or a material having at least one amino group selected from among primary, secondary, tertiary, and quaternary amino groups.

The material 28A may be obtained by modifying the surfaces of the microparticles 28 in various ways using organosilane. For instance, the organosilane may be coated on the surface of the microparticles 28 by a vapor phase deposition, self-assemble monolayer coating, or a combination thereof.

When the surfaces of the microparticles 28 include a material with an affinity to a specific or non-specific cell, the cells introduced into the first chamber 22 may be captured by the microparticles 28. In this state, the vibration of the membrane 26 may cause the microparticles 28 to move, and thus, to collide against each other or the inner wall of the first chamber 22. During this process, the cells captured by the microparticles 28 may be disrupted.

In some embodiments, after supplying the solution including the cells to be disrupted into the first chamber 22, a substance with an enhanced cell lytic effect may be supplied into the first chamber 22, followed by cell disruption. The substance may be a cell lysis solution. The cell lysis solution may include, for example, NaOH, KOH, a chaotrope solution, a surfactant, or the like. The cell lysis solution may be used in a concentration not affecting a post-process following the cell disruption, such as a polymerization chain reaction (PCR), so that the PCR may be conducted immediately after the cell disruption without additional purification. If the substance is used in a concentration affecting the PCR, additional purification may be carried out. The cell lysis solution may also be supplied after the cell disruption to facilitate the release of nucleic acid.

In some embodiments, after the supply of the solution including the cells to be disrupted into the first chamber 22, cell disruption may be carried out without additional supply of the cell lysis solution into the first chamber 22.

Figure 3:
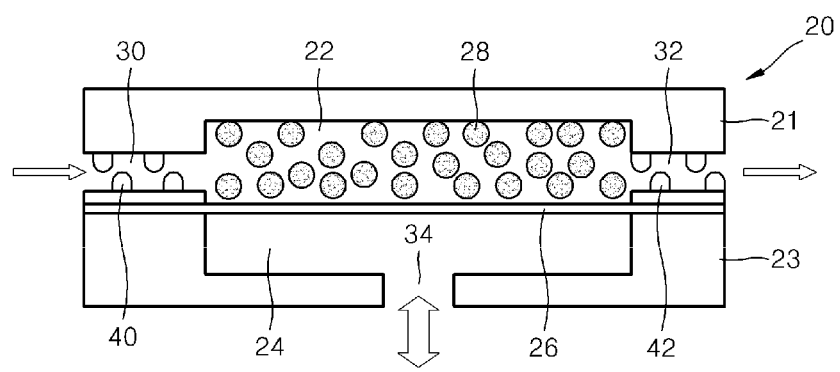
FIGS. 3 to 7 are cross-sectional views of microfluidic devices.

FIG. 3 illustrates an alternative form of the microfluidic device 20 of FIG. 1, according to an aspect of the present disclosure. Described hereinafter are only the portions not identical with those of the microfluidic device 20 of FIG. 1. This also applies to FIGS. 4-8.

Referring to FIG. 3, the inlet 30 and the outlet 32 may have a diameter larger than that of the microparticles 28. A plurality of first protrusions 40 may be distributed on an inner side of the inlet 30. The plurality of first protrusions 40 may be evenly distributed throughout the inner side of the inlet 30. The plurality of first protrusions 40 may be disposed to protrude in opposite directions. Due to the first projections 40, a substantial diameter or effective diameter of the inlet 30 may be smaller than the diameter of the microparticles 28. A plurality of second protrusions 42 may be distributed on an inner side of the outlet 32. The distribution of the second protrusions 42 may be identical with that of the first protrusions 40. Due to the second protrusions 42, a substantial diameter or effective diameter of the outlet 32 may be smaller than the diameter of the microparticles 28. The first protrusions 40 and the second protrusions 42 may be identical or different in shape. Instead of disposing the first and second protrusions 40 and 42, the inlet 30 and the outlet 32 may be formed to have an embossed inner side.

Figure 4:
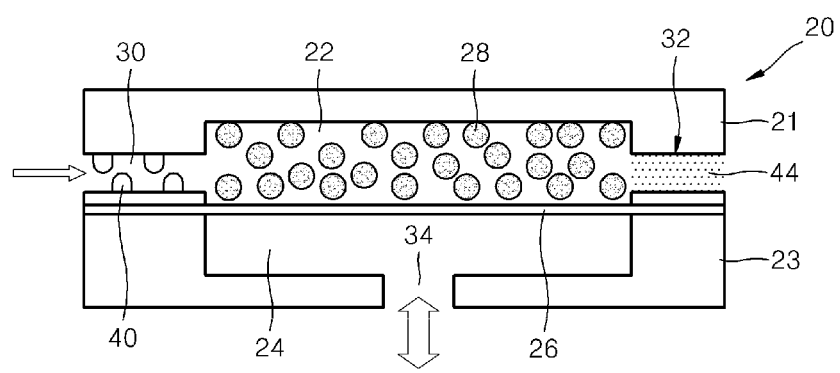

FIG. 4 illustrates another alternative form of the microfluidic device 20 of FIG. 1, according to an aspect of the present disclosure.

Referring to FIG. 4, structural features of the inlet 30 may be identical with those described in relation to FIG. 3. A filter 44 may be disposed in the outlet 32. The filter 44 may be a porous material that allows components of the disrupted cells to pass selectively or non-selectively. The inlet 30 may have a diameter smaller than that of the microparticles 28, as in FIG. 1. The porous material may be, for instance, a membrane filter having pores, such as a membrane filter manufactured from polyethylene, polypropylene, polybutylene, polystyrene, and polyacrylate, fiber or a combination.

Figure 5:
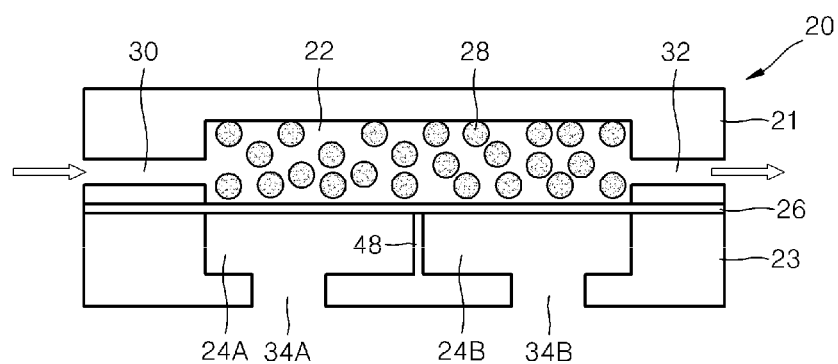

FIG. 5 illustrates another alternative form of the microfluidic device 20 of FIG. 1, according to an aspect of the present disclosure.

Referring to FIG. 5, two chambers, i.e., a third chamber 24A and a fourth chamber 24B, may be disposed in place of the second chamber 24 of FIG. 1. The third chamber 24A and the fourth chamber 24B may be separated by a partition wall 48. The role of the third and fourth chambers 24A and 24B may be the same as that of the second chamber 24 of FIG. 1. The third chamber 24A may include a first port 34A, and the fourth chamber 24B may include a second port 34B. The role of the first and second ports 34A and 34B may be the same as that of the port 34 of the second chamber 24. According to various embodiments, structural features of the inlet 30 and the outlet 32 may be identical with those described in relation to FIG. 3 or FIG. 4. A pressure may be applied simultaneously or sequentially to the first and second ports 34A and 34B to simultaneously or sequentially vibrate portions of the membrane 26 defining the third chamber 24A and the fourth chamber 24B. A pressure with a same or different phase may be applied to the first and second ports 34A and 34B to vibrate the membrane 26 in each chamber at a same or different phase. For example, a positive pressure may be applied to the first port 34A, while a negative pressure is applied to the second port 34B to vibrate the membrane 26 in the third chamber 24A and the membrane 26 in the fourth chamber 24B at opposite phases.

Figure 6:
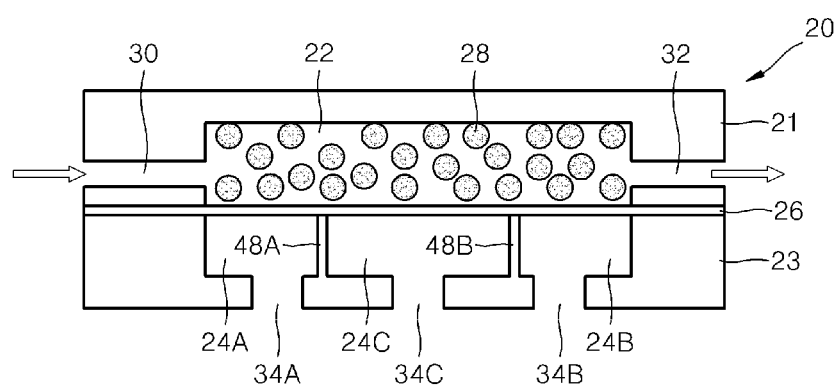

FIG. 6 illustrates another alternative form of the microfluidic device 20 of FIG. 1, according to an aspect of the present disclosure.

Referring to FIG. 6, three chambers, i.e., third, fourth, and fifth chambers 24A, 24B, and 24C, respectively, may be disposed in place of the second chamber 24 of FIG. 1. The role of the third to fifth chambers 24A, 24B, and 24C may be the same as that of the second chamber 24 of FIG. 1. The third and fifth chambers 24A and 24C may be separated by a first partition wall 48A. The fourth and fifth chambers 24B and 24C may be separated by a second partition wall 48B. The third to fifth chambers 24A, 24B, and 24C may have first to third ports 34A, 34B, and 34C, respectively. The role of the first to third ports 34A, 34B, and 34C may be the same as that of the port 34 of the second chamber 24. Although the embodiment of FIG. 6 illustrates the division of the second chamber 24 of FIG. 1 into three chambers, the second chamber 24 of FIG. 1 may be divided into more than three chambers. A pressure may be applied simultaneously or sequentially to the first to third ports 34A, 34B and 34C to simultaneously or sequentially vibrate the membrane 26 defining each chamber. A pressure with a same or different phase may be applied to the first to third ports 34A, 34B and 34C to vibrate the membrane 26 in each chamber at a same or different phase. For example, a positive pressure may be applied to the first and third ports 34A and 34C, while a negative pressure is applied to the second port 34B to vibrate the membrane 26 in the third and fifth chambers 24A and 24C and the membrane 26 in the fourth chamber 24B at opposite phases.

In other embodiments, the roles of the first and second chambers 22 and 24 in FIGS. 1, and 3 to 6 may be switched. That is, either one of the first and second chambers 22 and 24 may includes microparticles 28, and the other chamber may be used as a chamber into which a fluid for pressurization is introduced. If the second chamber 24 is used as a chamber into which a fluid for pressurization is introduced, the port 34 of the second chamber 24 may be connected to a pressure controller (not shown) that is able to pressurize or depressurize the interior of the second chamber 24. This may also apply to the third to fifth chambers 24A, 24B, and 24C.

Using the above-described method of processing a target material in a sample, a target material in a sample may be efficiently processed. The process of the target material may include binding, washing, and drying of the target material, and a combination thereof. When the target material is a cell and/or a biological material, the process may include binding, washing, drying and disrupting of the cell, and separating of the biological material. According to the above-described embodiments of the present disclosure, an SVR of the chamber filled with the solid supports may be controlled by utilizing deflection of the elastic membrane to enhance interaction between the surfaces of the solid support and the target material in the sample.

According to another aspect of the present disclosure, a microfluidic device is provided, which is useful in the foregoing method or for any other purpose. The microfluidic device includes a first chamber with an inlet and an outlet, a second chamber operatively connected with a pressure supply unit, and an elastic membrane disposed between the first chamber and the second chamber and forming a wall of at least part of the first and second chambers, where the first chamber includes a a material capable of binding to a target material. The microfluidic device may also comprise a pressure supply unit for providing a driving force to move fluid operatively connected to the first chamber. The microfluidic device may include at least one reservoir connected to the first chamber in fluid communication therewith. The reservoir may be at least one of a wash solution reservoir, an eluent reservoir, and a pH adjustor reservoir.

All other aspects, parts, and features of the microfluidic device are as described in connection with the method of processing a target material. Detailed descriptions of the same parts as those described above in connection with the microfluidic device used in the method of processing a target material in a sample are not be provided to avoid redundancy.

The microfluidic device may further comprise a pressure controller operatively connected to the second chamber for controlling application of a positive pressure to the second chamber to extend the elastic membrane toward the first chamber, or application of a negative pressure to the second chamber to extend the elastic membrane toward the second chamber.

The pressure controller may comprise a signal storage medium, wherein the signal storage medium comprises a signal for enabling application of the positive pressure to the second chamber to extend the elastic membrane toward the first chamber in a sample introduction operation and a washing solution introduction operation, and a signal for enabling application of a negative pressure to the second chamber to extend the elastic membrane toward the second chamber in a cell lysis operation, when a sample comprises a cell.

The pressure controller may comprise a signal storage medium, wherein the signal storage medium comprises a signal for enabling application of a positive pressure to the second chamber to extend the elastic membrane toward the first chamber in a sample introduction operation, a washing solution introduction operation, and a target material elution operation, when the sample comprises a nucleic acid, protein, or sugar as the target material.

The present disclosure will be described in further detail with reference to the following examples. These examples are for illustrative purposes only and are not intended to limit the scope of the disclosure.

1. Materials and Methods

The materials and methods used in these examples were as follows unless otherwise specified.

(1) Cells and Culture

Methicillin-resistant staphylococcus aureus (MRSA) strains used in the following examples were MRSA with accession No. ATCC BAA-1717 (MREJ Type ii), NCTC 13395 (MREJ Type v), and JCSC 3624 (MREJ Type xii). These MRSA strains were grown overnight in a 50-mL trypticase soy broth (TSB) (Becton, available from Dickinson and Company) at 37° C., washed twice with a 1× PBS solution (pH 7.4), and then suspended to an appropriate concentration of about 0.2 OD (optical density), which was equivalent to about $10^8$ CFU (colony forming unit)/mL.

(2) Manufacture of Microfluidic Device, Experimental Tools, and Bead Surface Modification (2.1) Manufacture of Microfluidic Device A microfluidic device was manufactured to include a common elastic membrane between two glass chips. The first and second glass chips with partial or whole of each chamber and each channel were bound together with the elastic membrane therebetween, thereby completing the manufacture of a bead-packed microfluidic device.

In the current example, the first and second glass chips were manufactured by defining channels and chambers in glass wafer by common photolithography, etching, and wet-etching processes. After being cleaned with a piranha solution, a 6-inch glass wafer (borosilicate, 700 μm thick) was deposited with a 500-nm thick polysilicon layer by low-pressure chemical vapor deposition (LPCVD). Then, a patterning process was performed to expose a part of the deposited polysilicon layer exposed through a photoresist film. The exposed part of the polysilicon layer was removed by dry etching. Afterwards, the photoresist film was stripped off, and the exposed glass wafer was wet-etched with a hydrofluoric acid solution (HF 49%) to form a channel having a depth of about 100 μm and a width of about 100 μm. In the etching process for forming the channel, a weirs (protrusions) of about 20 μm was formed to confine beads. The weir was formed to serve both as a valve seat and a bead trapping weir.

Then, after the polysilicon layer was removed, a dry film resist (DFR) was coated and patterned. Then, a chamber including beads (ca. about 15.5 μL). and holes for fluid inflow or outflow were formed using a sand-blasting method. Subsequently, the glass wafer was diced into chip-shaped pieces, which were then washed using plasma. A fluidic chip ("first glass chip") including the above-manufactured chamber to accommodate beads, and a pneumatic chip ("second glass chip") including a chamber to function as a pneumatic pump not including beads were permanently coupled with an about 250-μm thick PDMS membrane (available from Rogers) activated with plasma between the first and second glass chips as an intermediate layer. The PDMS membrane, a monolithic flexible membrane, was used to control fluid flow and as a pump and valve and an actuator for inducing collisions between beads by pneumatic vibration.

Unless otherwise specified, about 15-16 milligrams (mg) (about $2\times10^5$ in number) surface-modified glass beads were put into the bead chamber, which was then sealed using a PCR-compatible adhesive tape (available from Applied biosystems). The attached tape was covered with a polycarbonate plate to prevent the tape from bending during operation such as a deoxyribonucleic acid (DNA) extraction. The surface-modified glass beads may be directly put into the bead chamber.

Operation of the PDMS membrane was controlled by applying a positive pressure or a negative pressure to the pneumatic chamber with a Solenoid valve array (S070-5DC, available from SMC) connected thereto. The valves were coupled to an electro-pneumatic-regulator (ITV0030-3BL, available from SMC) and LabVIEW software (available from National Instruments). Operation of the valves associated with fluid transfer was visualized through an interface of the LabVIEW software in each step to monitor extraction of nucleic acids.

Figure 7:
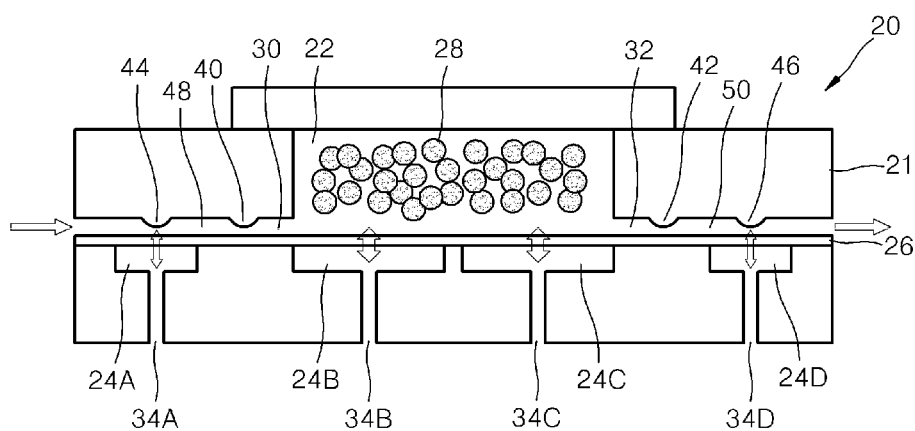
Figure 8:
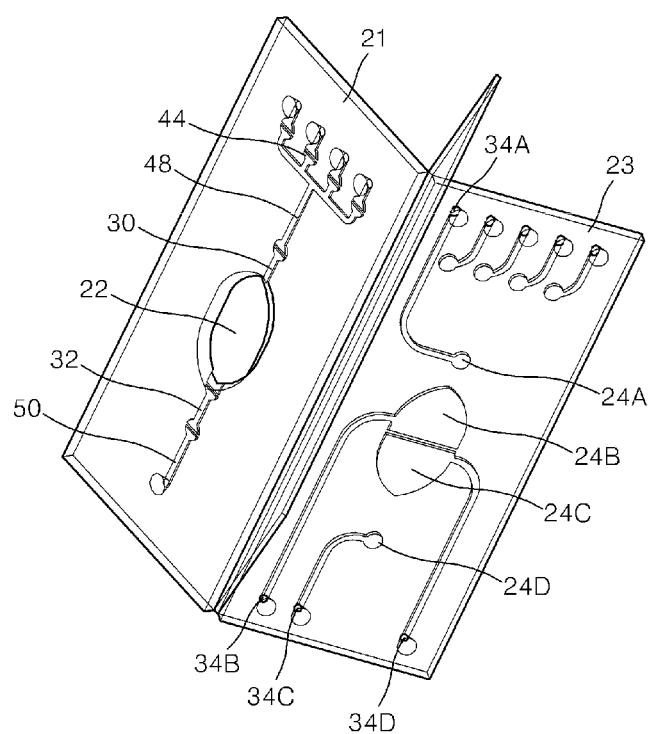
FIG. 8 is an enlarged view of a 3-layered microfluidic device including monolithic glass, PDMS and glass, and fluidic and pneumatic components.

FIGS. 7 and 8 illustrate a microfluidic device according to an embodiment of the present disclosure, used in the method of processing a target sample in a sample. FIG. 7 is a cross-sectional view of a bead-packed microfluidic device in which collisions of beads are induced by vibration of a PDMS membrane, according to an aspect of the present disclosure. Referring to FIG. 7, an inlet 30 with a protrusion 40 and an outlet 32 with a protrusion 42 are connected to an inlet port and an outlet port, respectively, via fluid channels 48 and 50. Valve seats 44 and 46 are formed in an upper plate defining the inlet 30 and the outlet 32, respectively. Pneumatic chambers 24A and 24D are formed in a lower plate to correspond to the valve seats 44 and 46, respectively. A bead-packed first chamber had a volume of about 15.5 uL and dimensions of about 6 mm×about 4 mm×about 0.75 mm (largest length×smallest length×depth). Two displacement pneumatic chambers each had a total volume of about 3 uL, and dimensions of about 6 mm×about 4 mm×about 0.2 mm (largest length×smallest length×depth).

FIG. 8 is an enlarged view of a 3-layered microfluidic device including monolithic glass, PDMS and glass, and fluidic and pneumatic components of the microfluidic device, according to an aspect of the present disclosure.

(2.2) Glass Bead Modification

After being washed with a piranha solution and then with deionized water, glass beads having a diameter of about 30 μm to 50 μm (available from Polysciences, Inc.) were filtered and vacuum-dried.

Afterwards, a 5% (v/v) trimethoxysilylpropyl-modified polyethyleneimine solution (available from Gelest, Inc.) in ethanol was prepared as a bead-surface modification solution. The beads were put into the bead-surface modification solution and reacted for about 2 hours with gentle mixing, followed by filtration and washing with fresh ethanol three times. The final recovered glass beads were heated in a 110° C. oven for 40 minutes, to obtain glass beads having surfaces coated with polyethyleneimine (PEIM). PEIM is known to be able to nonspecifically bind to cells, and thus the glass beads coated with the PEIM may be used to nonspecifically separate cells.

(3) Measurement of Cell Release Efficiency Using Swab

Two commercially available swabs, i.e., flocked swab (Cat. No. 553C, Copan) and fiber swab (Cat. No. 220099, BBL™ CultureSwab™, BD) were used to determine cell release efficiency.

A MRSA suspension (1× PBS buffer, pH 7.4) of a known concentration was continuously diluted to a concentration of about $10^3$ CFU/mL. A 100 μL fraction therefrom was added into a PBS buffer of about 900 ul in 1.5 mL-microcentrifuge tubes. This solution was smeared on a Petrifilm (3M, USA) as an initial MRSA cell number. The swabs were put into a 1 mL MRSA suspension (about $10^3$ CFU/ml, a volume of absorbed liquid was about 100 μL), followed by vortexing in a 1 mL fresh PBS buffer for about 1 minute. This solution including the released MRSA was smeared on a Petrifilm as a recovered MRSA cell number. These processes were performed three times for each swab in each of three different manufacturing lots. The resulting products were Incubated at about 37° C. for about 24 hours, followed by colony counting. A cell release efficiency was calculated by dividing a total number of the recovered bacteria colonies by the number of initial bacteria colonies. Cell capture efficiency was determined by counting colonies before and after the solution was passed through the bead-packed microfluidic device.

(4) DNA Extraction Efficiency from MRSA in Nasal Swab

After pooling a negative nasal swab, MRSA was spiked to prepare MRSA-positive samples for analytical tests. Specimens were collected from anterior nares of healthy volunteers using dried flocked swabs. The collected swab was pooled in a sodium phosphate buffer (PBS) (50 mM, pH 3.0, Sigma-Aldrich), followed by vortexing for 1 minute to simulate MRSA release (negative control matrix; negative nasal matrix). A volume of the negative control matrix was adjusted to include 1 swab per 1 mL. Other dried swabs were made wet with an MRSA suspension of a known concentration to obtain simulated positive MRSA swabs. Swab stems were broken, and then vortexed to release absorbed MRSA into 1 mL of the negative nasal matrix.

The resulting MRSA-positive nasal swabs were passed through an Isopore™ membrane filter (available from Millipore) having a pore size of about 3 um. 1 mL of the filtered MRSA-positive nasal swab, 0.5 mL of a Tris-EDTA buffer (10 mM, pH 8, Ambion) for washing, and 10 μL of a NaOH solution (0.02 N, Sigma-Aldrich) for cell lysis were previously distributed into liquid reservoirs of the microfluidic device.

The liquid solution was transferred by performing pressure-driven operation. An operating liquid pressure was determined through a preliminary test. The nasal swab solution was passed through the bead-packed first chamber at a flow rate of about 200 μL/min at about 50 kPa while the PDMS membrane was pressurized toward the first chamber by applying a positive pressure of about 150 kPa to the second chamber. After initial sample loading, while the PDMS membrane was extended toward the first chamber, a wash solution (Tris-EDTA buffer (10 mM, pH8, Ambion)) was flowed at a flow rate of about 500 μL/min at about 80 kPa to wash the first chamber, and nitrogen air was then flowed for drying at about 100 kPa for about 30 seconds.

To lyze the captured cells, while the PDMS membrane was displaced toward the second chamber (at about −150 kPa), 6 μL of a NaOH solution was injected, and valves near the inlet and outlet of the bead-packed first chamber were closed.

Next, two pneumatic displacement chambers, i.e., the first chamber and the second chamber, were controlled to have asymmetrically alternating pressures, i.e., so that a positive pressure of about 80 kPa was applied to one of the chambers and a negative pressure of about −80 kPa was applied to the other chamber for a first half of one cycle, and these pressures were reversed for a second half of the cycle. The PDMS membrane was vibrated at a frequency of about 10 Hz for about 5 minutes to induce cell lysis.

DNA-included lysed cell products were eluted by injection of a 4 µL NaOH solution at a liquid pressure of about 100 kPa while the PDMS membrane was displaced toward the first chamber at a pressure of about 150 kPa.

The time taken in the overall processes from the introducing of the liquid sample, to the DNA elution was less than about 20 minutes. No additional DNA purification was performed. To measure analytical sensitivity of the microfluidic device, an experiment was conducted on three types of MRSA strains having at least seven replicates for each concentration (10, 20, 100 and 200 CFU/swab). According to the number of positive calls determined using an PCR instrument (i.e., a Ct cutoff value of 40), analytical sensitivities at a 95% confidence interval were estimated using statistical analysis using a probit regression model (MINITAB™ Release 14.20).

Figure 9:
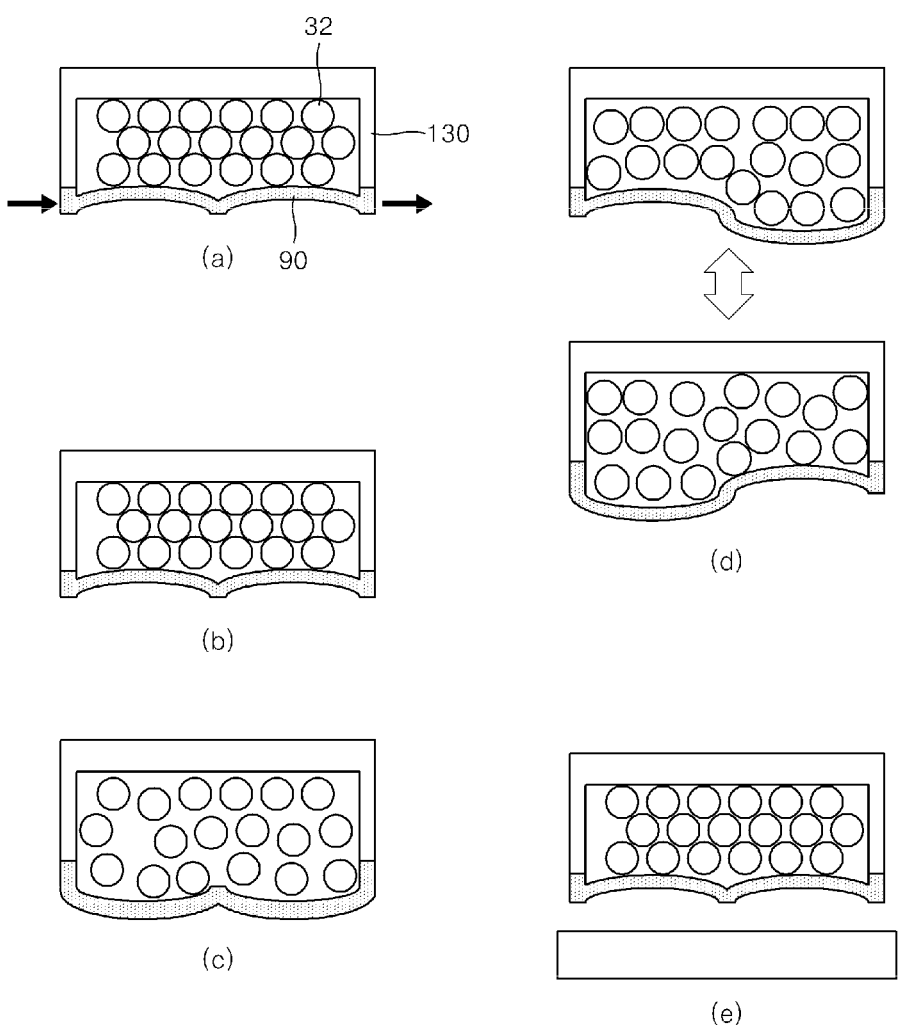
FIG. 9 is a schematic diagram of a method of processing a target material in a sample by using the microfluidic device of FIGS. 7 and 8, illustrating operations from cell capture from the sample to nucleic acid elution.

FIG. 9 is a schematic diagram of a method of processing a target material in a sample, according to an embodiment of the present disclosure, covering the entire processes from a sample introduction operation to a DNA release operation. In FIG. 9, (a) illustrates introducing the sample including a cell to bind the cell to the beads, i.e., a cell capture operation. The captured cell may be (b) washed and/or dried. Next, (c) a cell lysis solution may be introduced into the washed and/or dried first chamber. In the embodiment shown, (d) illustrates mixing the introduced cell lysis solution and beads through asymmetrical vibration of the PDMS membrane to lyze the cell. In the embodiment shown, (e) illustrates releasing DNA from the first chamber including the lysed cell products. In some embodiments, at least one of the washing, drying, and cell lysis solution introduction operations may be omitted. For example, without performing the washing, drying and cell lysis solution introduction operations, the cell bound to the beads may be lyzed by vibration of the PDMS membrane. In some other embodiments, the washing, drying, or cell lysing solution introduction operation may be omitted. In FIG. 9, a partial structure of the microfluidic device of FIG. 9 is omitted for simplification.

For comparison with a Ct value of an experimental group, a positive control group having a Ct value was prepared. A MRSA suspension in a PBS buffer was centrifuged at about 13,200 rotations per minute (rpm) for about 20 minutes, and the supernatant was removed therefrom. A remaining cell pellet was processed using a table-top bead-beating instrument (GENIE 2, available from Fisher Scientific). 30 mg of bare glass beads and about 10 µL of a cell lysis solution (0.02N, NaOH) were added to the cell pellet, followed by vigorous vortexing at a full speed for about 5 minutes. After simple centrifugation, a solution of released DNA was recovered. For accurate comparison, the number of injected cells and eluate volume were controlled to be the same in the two methods.

(5) DNA Amplification by Real-Time PCR

To evaluate analytical behavior, real-time polymerase chain reaction (PCR) assays were performed using a LightCycler™ 480 real-time PCR system (available from Roche).

To identify a MRSA, sequences of junction regions of a staphylococcal chromosomal cassette (SCCmec) adjacent to an integration site called SCCmec Right Extremity Junction (MREJ) and an orfX region were specifically amplified. A used specific primer set designed by using Primer3 software (Whitehead Institute/MT Center for Genome Research) was as follows: MREJ type ii (forward; SEQ ID No. 1 and reverse; SEQ ID No. 2), type v (forward; SEQ ID No. 3 and reverse; SEQ ID No. 4), and type xii (forward; SEQ ID No. 5 and reverse; SEQ ID No. 6).

A PCR reaction mixture was prepared to have the following composition; 0.4 µM TaqMan probe (FAM-5'-aga Gca Ttt Aag Att Atg cg (SEQ ID No. 7)-3'-BHQ1, wherein capital letters indicate LNA bases, Sigma), 1 µM of each primer (Sigma), 1× LightCycler™ 480 Probes master mix (Roche), and 4 µL of an extracted-DNA solution. After pre-denaturation for about 10 minutes, thermal cycling was conducted as follows: denaturation at 95° C. for 20 minutes and elongation at 60° C. for 40 seconds.

PCR amplified products of MREJ types ii, v, and xii were about 91 bp, 96 bp, and 89 bp, respectively, which were confirmed by electrophoresis (Agilent 2100 Bioanalyzer, available from Agilent Technologies).

(6) Simulation of PDMS Membrane Deflection

Figure 10:
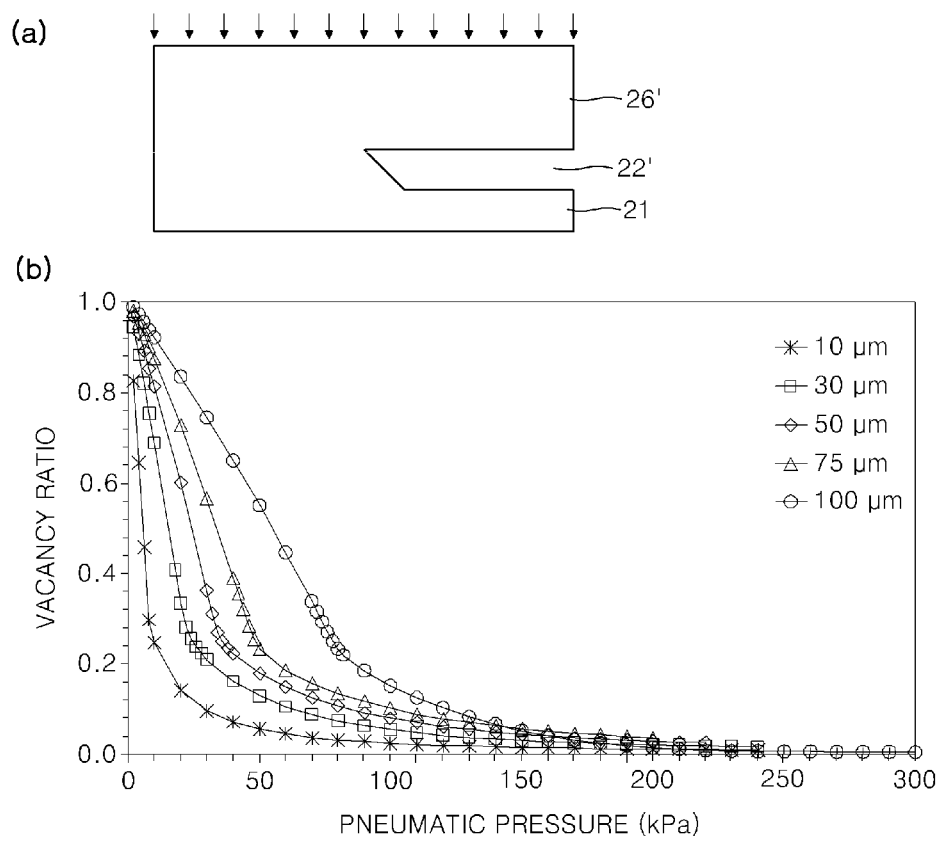
FIG. 10a illustrates an experimental model used in investigating effects of deflection of a polydimethylsiloxane (PDMS) membrane on a bead packing ratio of a chamber.
FIG. 10(b) is a graph of the vacancy ratio plotted against pneumatic pressure showing the results of the investigation.

To investigate effects of deflection of the PDMS membrane on bead packing, a simple axisymmetric model of a microfluidic device illustrated in (a) of FIG. 10 was used.

Uniform pneumatic pressure load conditions (34) were defined at the upper boundary of the PDMS membrane. Y-directional zero-displacement conditions were defined at the left boundary, and x-directional and y-directional zero-displacement conditions were defined at the lower boundary. The thickness of the PDMS membrane (21) was fixed to about 250 µm, while the chamber depth (22) was varied from about 10 um to about 100 µm. The lower plate (23) was a glass.

This model was created using a Stress and Grid Deformation module in CFD-ACE+ (ver. 2009, ESI Group, France) with a pneumatic increment of about 10 kPa from 0 kPa to 300 kPa. Referring to (b) in FIG. 10, the increment was found to reduce to about 2 kPa in the initial condition (0-10 kPa) and near a contact range between the PDMS membrane and glass. The pneumatic increment was terminated when an element having a negative volume was generated. The standard first element was used, and total numbers of nodes and elements were 3815 and 3649, respectively.

Characteristics of the material used in the simulation test were as follows:

PDMS; Density=970 kg/m$^3$, Young's modulus of elasticity=750 kPa,
Poisson's ratio=0.5,
Glass: density=2520 kg/m$^3$,
Young's modulus of elasticity=80 GPa,
Poisson's ratio=0.3.

Example 1

Bead Packing Ratio and Cell Capture Efficiency

In the present example, effects of deflection of the PDMS membrane on the bead packing ratio were investigated.

FIG. 10 illustrates an experimental model (a) used in investigating effects of deflection of the PDMS membrane on the bead packing ratio, and results (b) of the investigation. The experiment was conducted as described in (6). In (b) of FIG. 10, the vacancy ratio is defined as a result of dividing a void volume with zero displacement caused by the PDMS membrane by the initial chamber volume. Referring to (b) in FIG. 10, the vacancy ratio was remarkably reduced as the PDMS membrane was deflected without contacting the chamber. After a contact between the PDMS membrane and the chamber, due to gradual deflection at an edge part of the PDMS membrane and partial compression at a central part thereof, the vacancy ratio was gradually reduced. When the pressure was increased above 100 kPa, the vacancy ratio was mostly less than 10%. These results indicate that most of the glass beads were randomly close-packed due to the pneumatic deflection of the PDMS membrane.

A degree of bead packing may be influenced from a membrane condition and bead amount. Therefore, in the present example, effects of a membrane condition and bead amount on cell capture were measured and investigated. The results indicate effects of the bead packing ratio on cell capture.

Table 1 is a table of results from the measurement of the effects of a membrane condition and bead amount on SVR ($\mu m^{-1}$) and cell capture.

TABLE 1

| Bead amount (mg) | Upward pressurization | | Rest condition | |
|---|---|---|---|---|
| | SVR ($\mu m^{-1}$) | Capture efficiency (%) | SVR ($\mu m^{-1}$) | Capture efficiency (%) |
| 10 | 0.15 | 95.1 ± 1.2 | 0.05 | 37.2 ± 5.9 |
| 13 | 0.15 | 97.0 ± 1.3 | 0.08 | 60.8 ± 6.4 |
| 16 | 0.15 | 97.8 ± 0.6 | 0.11 | 87.2 ± 4.4 |

The results in Table 1 were obtained using 1 mL of MRSA (ATCC BAA-1717, $10^6$ CFU/ml) in sodium phosphate (50 mM, pH 4.0), wherein the measurement for each condition was performed three times.

Referring to Table 1, with a decrease in bead amount from about 16 mg to about 10 mg (reduction by about 38%), a total bead surface area was reduced in proportion to the reduction in bead amount. However, when pressurized upward (i.e., toward the first chamber), the PDMS membrane had a constant SVR of about 0.15 $\mu m^{-1}$ independent from the bead amount. SVR was calculated with the assumption that the beads had a uniform diameter of about 40 $\mu m$ and a close-packing ratio of about 50%. The cell capture efficiency and standard deviation were found to be better when the PDMS membrane is pressurized upward, as compared with those the PDMS membrane is in a rest condition.

These results indicate that pneumatic induction of bead close-packing is effective to increase the SVR, facilitating interaction between a liquid solution and the bead surface, so that analytical behavior of target material may be improved. SVR is a more significant variable than surface area in solid-phase extraction. The cell capture efficiency was found to be higher when the bead amount was about 10 mg and the SVR was about 0.15 $\mu m^{-1}$, as compared with when the bead amount was about 16 mg and the SVR was about 0.11 $\mu m^{-1}$.

Adjustment of the bead packing ratio may be achieved by control of the flexibility of the elastic membrane used in the method of the present disclosure, or by control of the bead amount.

Example 2

Influence of PDMS Membrane Vibration on Small Volume Release of DNA

According to a conventional method, solid-phase DNA isolation was performed on a stationary phase as in chromatographic separation, and accordingly, target DNA was collected from a time-dependent eluate fraction. Since a separation column was stationary, mass transport between liquid and the solid support was exclusively diffusion-dependent. Therefore, it was difficult to release a small elutate volume (≤10 $\mu L$) of DNA on the solid phase surface for appropriate use in an increased concentration in a subsequent detection process such as PCR. A small eluate volume is used to increase the number of target copies per volume to attain high detection sensitivity.

Therefore, in the present example, effects of PDMS membrane's vibration on the small volume release of DNA were investigated. In particular, to capture cells, 1 mL of each of two MRSA suspensions in different concentrations (ATCC BAA-1717, $10^3$ CFU/ml and $10^5$ CFU/ml) was introduced into a bead-packed chamber of a microfluidic device. A cell capture process was performed in the same manner as described in (4) (bead amount 16 mg). During this process, the bead-packed column was vigorously agitated by vibrating the PDMS membrane while not losing inherent characteristics of the bead-packed column, i.e., thereby even capable of inducing disruption of the cell wall ((d) in FIG. 9). To facilitate introduction of 6 uL of a NaOH solution for lysing the cells bound to the bead surfaces, the PDMS membrane was pressurized downward to increase the void volume of the bead chamber by about 3 $\mu L$ (i.e., (c) in FIG. 9), followed by asymmetrical vibration of the PDMS membrane to induce disruption of the cell wall and release DNA from the cells or bead surfaces.

To determine a DNA recovery ratio from the captured cells, after recovery of the 6 $\mu L$ liquid fraction first used in the vibration of the PDMS membrane, additional liquid fractions each of 6 $\mu L$ were further continuously passed through the first chamber. A DNA amount in each of the fractions was estimated using real-time PCR amplification.

Figure 11:
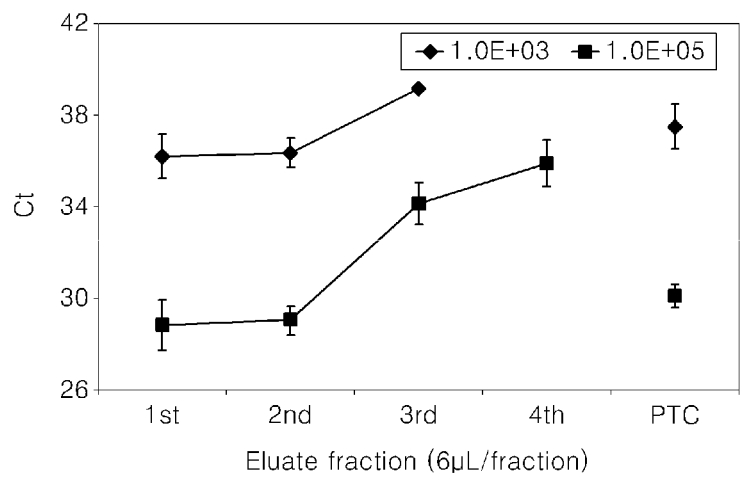
FIG. 11 is a graph of eluted DNA amount (Ct) according to each eluate fraction.

FIG. 11 is a graph of DNA amount (Ct) with respect to an eluate fraction. Referring to FIG. 11, the first two fractions were found to have less Ct value as compared with the other fractions by about 3 Ct. If PCR efficiency is 100%, a 10-fold difference in the number of initial DNA template copies may lead to a difference in Ct value by 3.3. Therefore, the results of FIG. 11 indicate that most of the DNA (about 90%) is released out of the bead-packed chamber using a 12 $\mu L$ eluate solution. Therefore, 100-fold volume reduction (i.e., 10 $\mu L$ of DNA eluate solution obtained from a 1 mL nasal swab sample used in the initial stage) may lead to a considerable increase in DNA amount, which may have a positive effect on detection sensitivity. Referring to FIG. 11, no DNA was detected in the fourth fraction of the sample ($10^3$ CFU/ml). A positive control (PTC) group was obtained through centrifugation and subsequent table-top-bead-beating disruption using 24 $\mu L$ of NaOH solution. 1 $\mu L$ of DNA solution was used as a template in PCR. The experiment was performed three times for each condition.

Example 3

MRSA Detection in Nasal Swab

In the present example, total DNA extraction was performed using MRSA in a nasal swab. All processes involved swabbing, cell release from the swab, pre-filtration, and sample loading onto a bead-packed chamber of a microfluidic device for DNA extraction. As a result of a preliminary experiment, flocked type swabs were found to have better cell release efficiency and less variation between products, as compared with fiber type swabs. For this reason, flocked type swabs were used in the present example.

In particular, a MRSA-spiked nasal swab was pre-filtered to prevent clogging of the microfluidic device by large impurities. Loss of MRSA by the pre-filtration was measured to be less than about 10% (which was verified by colony counting). All of the processes from swabbing to real-time PCR were successfully performed on MRSA in different concentrations ($10^4$, $10^3$, and $10^2$ CFU/swab).

Figure 12:
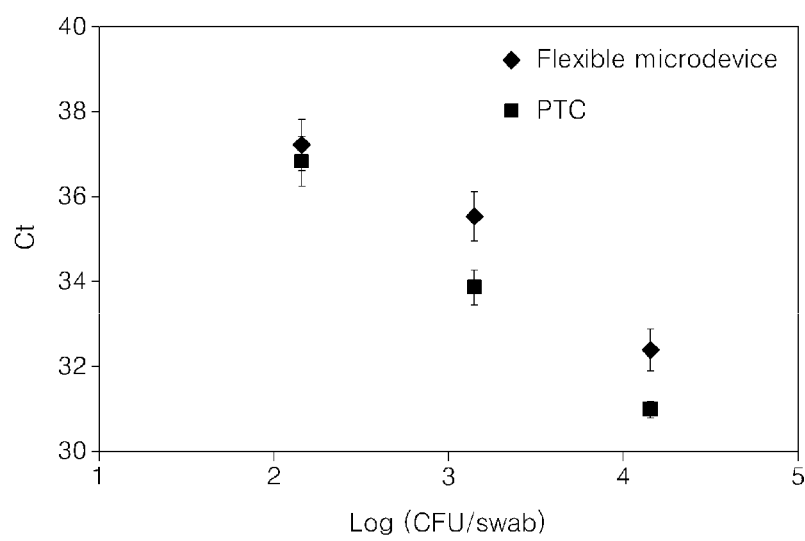
FIG. 12 is a graph of methicillin-resistant staphylococcus aureus (MRSA) detection (threshold cycle (Ct)) as a function of initial cell number (CFU/swab).

FIG. 12 is a graph of nucleic acid separation results with respect to an initial concentration of MRSA, according to an aspect of the present disclosure. That is, FIG. 12 shows results of detection of MRSA (NCTC 13395) in swabs with respect to initial cell counts (CFU/swab). DNA separation was performed in the same manner as described in the above Materials and Methods section. The DNA was eluted using a total of 10 μL of NaOH solution, and 4 uL of the elutate was used as a template in PCR along with a positive control (PTC) group.

No amplification product was found in a non-MRSA-spiked negative nasal matrix. The PTC group was prepared from an MRSA suspension in PBS without release and pre-filtration of MRSA from a swab. In particular, centrifugation of the MRSA suspension was followed by table-top bead beating disruption using 10 μL of NaOH solution to obtain the PTC group. When the PTC group was prepared from nasal swabs as in the experimental group, PCR amplification was significantly prohibited by concentrated impurities resulting from the centrifugation and subsequent cell disruption using a small volume of solution (10 μL).

This result indicates that the PCR inhibitors may be removed through flow-through cell capture and washing operations in a microfluidic device used in the method according to the one or more embodiments of the present disclosure, so that detection of MRSA in the nasal swab may be successful.

In the present example, using three types of MRSA strains (MREJ types ii, v and xii) in different concentrations (10, 20, 100, and 200 CFU/Swab), analytical sensitivity (i.e., limit of detection) defined as the smallest CFU of a swab that is distinguishable from a negative control group with reproducibility was estimated.

Table 2 comparatively shows estimated analytical sensitivities in relation to three types of MRSA strains between the method of the present disclosure and other methods.

TABLE 2

| Method | Analytical Sensitivity (CFU/swab) | | | Analyte dilution rate (Swab/PCR) |
| --- | --- | --- | --- | --- |
| | MREJ Type v[a] | MREJ Type xii[b] | MREJ Type ii[b] | |
| Method according to the present disclosure | 54 | 47 | 61 | 0.4 |
| Xpert ™ SA nasal complete | 97 | 127 | 256 | — |
| NucliSENS EasyQ ™ MRSA | 200 | 182 | 227 | 0.02 |
| GeneOhm ™ MRSA ACP Assay | 130 | 386 | 576 | 0.004 |

In Table 2, MRSA in swabs (positive swabs) was released into a buffer solution (sodium phosphate, 50 mM)[a] or a negative nasal matrix[b].

Referring to Table 2, analytical sensitivities with respect to the tested three types of strains were estimated to be about 47-61 CFU/swab at a 95% confidence interval. The method according to the one or more embodiments of the present disclosure using the above-described microfluidic device led to similar or better results as compared with other commercially available MRSA detection methods. These behaviors were confirmed through comparison of analyte dilution rates (ADR) between the methods.

ADR indicates an analyte amount remaining in a final PCR product, that is, a theoretical amount of swab per application reaction. For example, in the method according to the one or more embodiments of the present disclosure, 1 mL of 1 swab was processed using a 10 uL eluent solution, and 4 uL of the eluate was used in a PCR, so that an ADR of 0.4 swab/PCR was obtained, which is effectively implemented by the introduction of an elastic or flexible membrane into the microfluidic device.

ADR may serve as a descriptive index of a theoretical analyte enrichment ratio in biological assays. Different analysis results may be obtained depending on the applied analytical processes (i.e., DNA extraction and amplification). However, a 10-fold to 100-fold difference (1-2 orders of magnitude) in basic ADR may considerably affect analytical sensitivity. This difference would result from the fact that other DNA preparation methods requiring multiple manual steps with traditional experimental tools such as centrifuge, table-top bead-beating machine, pipet, heat block, and tube, etc. will dilute target analyte. Taking full advantage of the inherent microscale dimension of micro device along with its dynamic properties of solid phase yielded such a high ADR value.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of processing a target material in a sample, the method comprising:
   introducing the sample into a first chamber of a microfluidic device, wherein the microfluidic device comprises a first chamber with at least one inlet and at least one outlet;
   a second chamber operatively connected with a pressure supply unit; and
   an elastic membrane disposed between the first chamber and the second chamber and forming a wall of at least part of the first and second chambers,
   wherein the first chamber comprises or contains a material that binds to a target material,
   applying a positive pressure to the second chamber causing the elastic membrane to be extended toward the first chamber, or applying a negative pressure to the second chamber causing the elastic membrane to be extended towards the second chamber, and
   vibrating the elastic membrane.

2. The method of claim 1, wherein the method further comprises washing, drying, and eluting the target material, and at least one of the introducing of the sample, the washing, drying, or eluting the target material is performed while applying a positive pressure to the second chamber thereby causing the elastic membrane to be extended toward the first chamber.

3. The method of claim 1, wherein the sample flows from the at least one inlet of the chamber through the at least one outlet.

4. The method of claim 3, wherein a flow rate of the sample is from about 10 μl/min to about 500 μl/min.

5. The method of claim 1, wherein, when the positive pressure or the negative pressure is not applied to the second chamber, the first chamber has a volume of from about 1 μL to about 100 μL.

6. The method of claim 1, wherein the first chamber has a surface-to-volume ratio (SVR) of about 0.05 $\mu m^{-1}$ or greater when a positive pressure is applied to the second chamber determined thereby causing the elastic membrane to extend into the first chamber, the SVR indicating a ratio of the surface area of the solid support to the volume of the first chamber.

7. The method of claim 1, wherein the target material is a cell, and the method further comprises, after introducing the sample to the first chamber,
   introducing a cell lysis solution into the first chamber while applying a negative pressure to the second chamber and causing the elastic membrane to be extended toward the second chamber, thereby lysing the target material bound to the solid support.

8. The method of claim 7, further comprising:
   vibrating the elastic membrane after the introducing of the cell lysis solution to facilitate cell lysis.

9. The method of claim 8, wherein, in the microfluidic device, the second chamber comprises a plurality of sub-chambers connected to the pressure supply unit, wherein the elastic membrane is disposed between the first chamber and the sub-chambers of the second chamber, and forms a wall of at least part of the first chamber and each sub-chamber of the second chamber.

10. The method of claim 7, further comprising:
    before the introducing the cell lysis solution into the first chamber, introducing a washing solution into the first chamber while applying positive pressure to the second chamber causing the elastic membrane to be extended toward the first chamber, thereby removing a material that is not bound to the solid support.

11. The method of claim 10, further comprising:
    after the introducing of the washing solution, flowing a gas from the at least one inlets of the first chamber through the at least one outlet while the elastic membrane is extended toward the first chamber by pressurizing the second chamber, thereby drying the solid support.

12. The method of claim 7, wherein the material binding to the target material is a material with a water contact angle of from about 70 degrees to about 95 degrees or a material having at least one amino group selected from among primary, secondary, tertiary, and quaternary amino groups.

13. The method of claim 7, wherein the negative pressure causes a surface-to-volume ratio (SVR) of about less than 0.05 $\mu m^{-1}$, the SVR indicating a ratio of the surface area of the solid support to the volume of the first chamber.

14. The method of claim 12, further comprising:
    introducing an eluent into the first chamber while the elastic membrane is extended toward the first chamber by applying a positive pressure to the second chamber, thereby releasing a nucleic acid from the first chamber including the solid support.

15. The method of claim 7, wherein
    the sample is introduced while applying positive pressure to the second chamber causing the elastic membrane to be extended to the first chamber;
    the sample comprises a cell and the target material is a cell, a nucleic acid, or a combination thereof;
    the material binding to the target material is a material with a water contact angle of from about 70 degrees to about 95 degrees, or a material having at least one primary, secondary, tertiary, or quaternary amino group;
    and the sample is introduced into the first chamber of the microfluidic device at a pH of from about 3.0 to about 6.0, and a salt concentration of from about 10 mM to about 500 mM;
    wherein the method further comprises, after introducing the cell lysis solution, introducing a washing solution into the first chamber while applying a positive pressure to the second chamber causing the elastic membrane to be extended toward the first chamber, thereby removing material that is not bound to the solid support; and
    introducing an eluent into the first chamber to release a nucleic acid from the including the solid support.

16. The method of claim 1, wherein the target material is a nucleic acid, and the sample is introduced while applying positive pressure to the second chamber causing the elastic membrane to be extended toward the first chamber; and the method further comprises, after introducing the sample to the first chamber, introducing a washing solution into the first chamber while applying positive pressure to the second chamber causing the elastic membrane to be extended toward the first chamber, thereby removing material that is not bound to the solid support; and introducing an eluent into the first chamber to release the nucleic acid from the solid support.

\* \* \* \* \*